United States Patent [19]

Tsuda et al.

[11] Patent Number: Plant 6,915

[45] Date of Patent: Jul. 11, 1989

[54] PETUNIA PLANT 'REVOLUTION PURPLEPINK'

[75] Inventors: Shinzo Tsuda; Hiroshi Hirabayashi, both of Yachiyo, Japan

[73] Assignees: Suntory Limited, Osaka; Keisei Rose Nurseries, Tokyo, both of Japan

[21] Appl. No.: 178,957

[22] Filed: Apr. 6, 1988

[30] Foreign Application Priority Data

Oct. 1, 1987 [JP] Japan ..... 2478

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Armstrong, Nikaido, Marmelstein, Kubovcik & Murray

[57] ABSTRACT

Disclosed herein is a decumbent type petunia plant having long stems and large leaves. The plant has abundant branching and a great profusion of blooms, and the whole bush remains in bloom for a considerable period of time. The flowers are single and large and the petals have a somewhat metallic luster and a vivid reddish purple color with strong reddish purple lines radiating from a small brilliant purple area closely proximate to a pale to light yellow green center portion. The plant is highly resistant to rain, heat, and drought.

4 Drawing Sheets

BACKGROUND OF THE VARIETY

The present invention relates to a new and distinct variety of petunia plant obtained from crossing a wild type of petunia plant (♀) native to Brazil and 'Recoverer White (♂)'.

Petunia is a very popular plant and is used for flower bedding and potting in the summer season. There are only a few varieties of the petunia plant which do not have an upright growth habit and which have a high resistance to rain, heat, and drought. Accordingly, this invention was aimed at obtaining a new variety of decumbent habit petunia plant having long stems and large blooms, the bush remaining in bloom for a considerable period of time, and a high resistance to rain, heat, and drought.

The new variety of petunia plant according to this invention originated from a crossing of a wild type of petunia plant native to Brazil as the female parent and 'Recoverer White' as the pollen parent, in June, 1985 at the Yachiyo Farm of Keisei Rose Nurseries, Inc., residing at 755 Ōwadasinden, Yachiyo-shi, Chiba-ken, Japan. From this crossing, 350 seedlings were obtained in 1986, from which 5 seedlings were selected, propagated by cutting, and then grown as a trial by flower bedding. Only one of the 5 resulting plants was selected. The botanical characteristics of the finally-selected plant were then examined, using a similar variety, male parent 'Recoverer White', for comparison, from the spring of 1987. As a result, it was concluded that this petunia plant is distinguishable from any other variety, whose existence is known to us, and this new variety of petunia plant was named 'Revolution Purplepink'.

In the following description, the color-coding is in accordance with the Horticultural Colour Chart of The Royal Horticultural Society, London, England (R.H.S. Color Chart), and the Inter-Society Color Council—Nation Bureau of Standards Color Name (ISCC-NBS Color Name). A color chart based on the Japan Color Standard for Horticultural Plant (JHS Color Chart) is also added for reference.

The female parent used in the breeding of 'Revolution Purplepink' is a wild type of petunia native to Brazil, the seeds of which were gathered at Gramado, Rio Grande Do Sul, Brazil and introduced to Japan in October, 1983. This wild type of petunia plant is presently maintained at the aforementioned Yachiyo Farm of the Keisei Rose Nurseries, Inc. The main botanical characteristics of this female parent are as follows.

Plant:

*Growth habit.*—Decumbent.

*Plant height.*—20 cm.

*Spreading area of plant.*—100–150 cm in diameter.

*Blooming period.*—May to August in the southern Kanto area, Japan.

Stem:

*Length from base.*—50–80 cm.

*Thickness.*—Main stem 2.0–3.0 mm; lateral stem 1.5–2.5 mm.

*Color.*—Strong yellow green (R.H.S. 144B–144C, JHS 3512–3513).

*Branching.*—Over-abundant.

*Pubescence.*—Many.

*Length of internode.*—1.0–2.0 cm before blooming; 1.5–3.0 cm during blooming.

Leaf:

*Phyllotaxis.*—Opposite both before and during blooming.

*Shape.*—Oval.

*Size (average).*—4.5–5.5 cm×2.5–3.5 cm.

*Thickness.*—0.4–0.5 mm.

*Color.*—Grayish olive green (R.H.S. 137A–137B, JHS 3716–3717).

*Pubescence.*—Few.

Flower: Opening obliquely upward.

*Type.*—Single.

*Shape.*—Funnel-shape, with five-fissured limb.

*Diameter.*—4.0–5.0 cm.

*Color.*—In the unopened stage (bud), dark reddish purple (R.H.S. 79B, JHS 8907–8909); when open, vivid reddish purple (R.H.S. 74A, JHS 9207), at full bloom, vivid reddish purple (R.H.S. 80A, JHS 8906).

*Reproductive organs.*—1 pistil and 5 stamens, both normal.

*Peduncle.*—0.9–1.2 mm in thickness, and 2.0–2.5 cm in length.

Physiological and ecological characteristics: High resistance to cold, relatively high resistance to heat, and moderate resistance to disease and pest.

'Recoverer White', used as the male parent in the breeding of this new variety 'Revolution Purplepink', is one of the Recoverer Series bred by the Sakata Seed Corp., Japan. The Recoverer Series includes 'Recoverer Scarletred', 'Recoverer Blue', and 'Recoverer Pink', and these plants are commonly characterized by a high resistance to rain. The main botanical characteristics of 'Recoverer White', are as follows.

Plant:

*Growth habit.*—Upright.

*Plant height.*—30–40 cm.

*Spreading area of plant.*—25–30 cm in diameter.

*Blooming period.*—April to September in the southern Kantō area, Japan.

Stem:

*Thickness.*—Main stem 5.0–7.0 mm; lateral stem 2.5–4.5 mm.

*Color.*—Strong yellow green (R.H.S. 144B–144C, JHS 3512–3513).

*Branching.*—Abundant.

*Pubescence.*—Normal.

*Length of internode.*—2.0–3.0 cm before blooming; 2.0–4.0 cm during blooming.

Leaf:

*Phyllotaxis.*—Verticillate before blooming; opposite during blooming.

*Shape.*—Oval.

*Size (average).*—4.5–5.0 cm×2.5–3.0 cm.

*Thickness.*—0.4–0.6 mm.

*Color.*—Strong yellow green to moderate olive green (R.H.S. 144A–146A, JHS 3507–3508).

*Pubescence.*—Few.

Flower: Opening obliquely upward.

*Type.*—Single.

*Shape.*—Funnel-shape, with five-fissured limb.

*Diameter.*—8.0–8.5 cm.

*Color.*—In the unopened stage (bud), pale yellow green (R.H.S. 4D–157A, JHS 3304–3303); both when open and at full bloom, greenish white (R.H.S. 155D–155C, JHS 3701).

*Reproductive organs.*—1 normal pistil having a strong yellow green (R.H.S. 144B–144C, JHS 3512) stigma, and 5 normal stamens each having a pale yellow (R.H.S. 161D, JHS 2503) anther and a greenish white (R.H.S. 157D, JHS 3501) filament.

*Peduncle.*—1.5–2.5 mm in thickness, and 2.5–3.0 cm in length.

Physiological and ecological characteristics: High resistance to rain, heat, and disease, and moderate resistance to pest.

This new and distinct variety of petunia plant, 'Revolution Purplepink', was asexually reproduced by cutting at the aforementioned Yachiyo Farm of Keisei Rose Nurseries, Inc., and the homogeniety and stability thereof were confirmed.

SUMMARY OF THE VARIETY

The new variety of petunia plant has a decumbent habit and long stems and large leaves, and thus is very different from a similar variety, 'Recoverer White' male parent, having an upright growth habit; the leaves being larger than those of 'Recoverer White'. The plant has abundant branching and a great profusion of blooms, and the whole bush remains in bloom for a considerable period of time, longer than the blooming period of 'Recoverer White'. The flowers are single and large, somewhat larger than 'Recoverer White', and the petals have a somewhat metallic luster and a vivid reddish purple color, which is clearly distinguished from the greenish white of 'Recoverer White', with strong reddish purple lines radiating from a small brilliant purple area closely proximate to a pale to light yellow green center portion. The plant is highly resistant to rain, heat, and drought.

DESCRIPTION OF THE VARIETY

Figure 1:
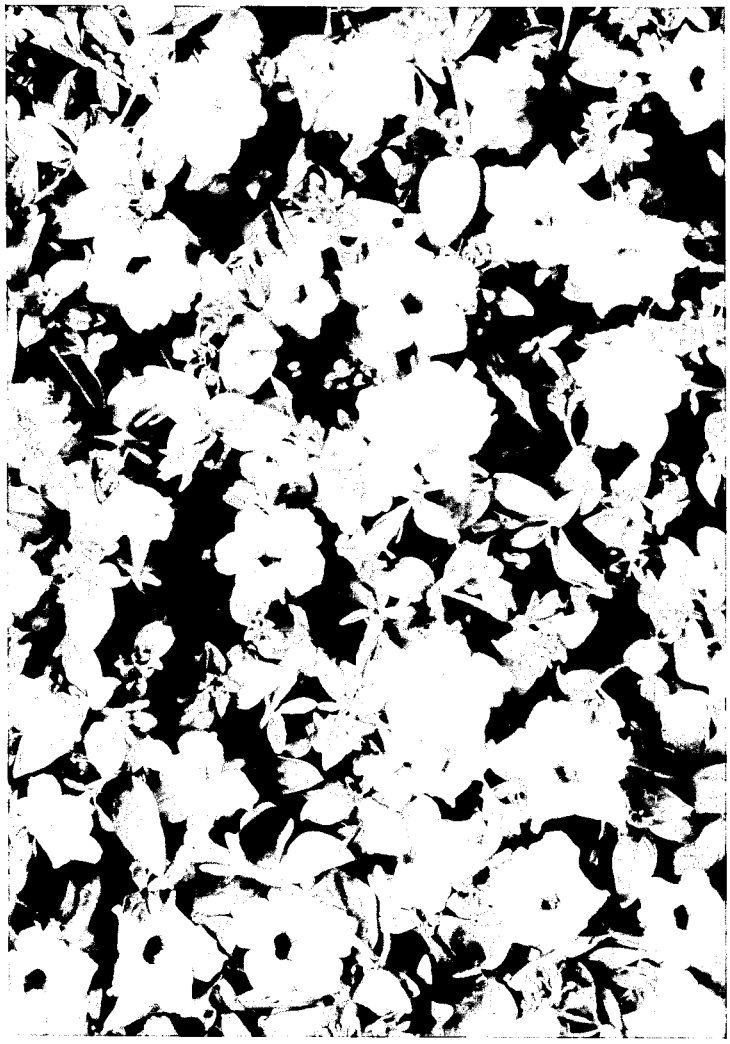
FIG. 1 is a photograph giving a partial view of the new variety of petunia plant planted in a flower bed.
Figure 2:
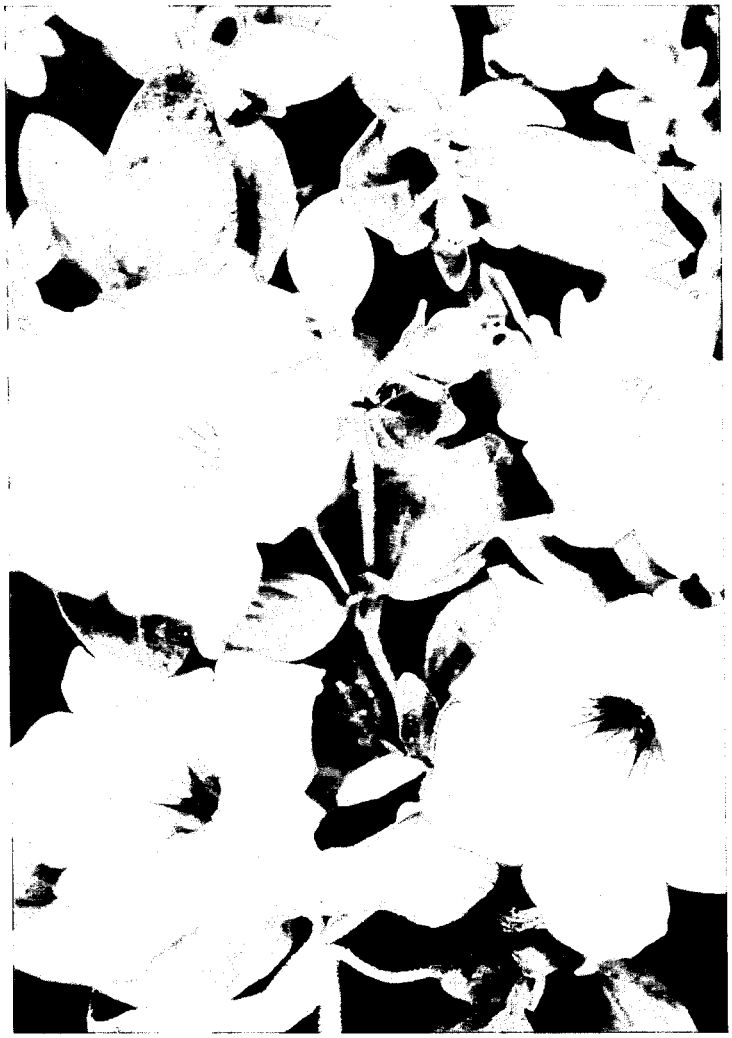
FIG. 2 is a photograph of flowers of the new variety of petunia plant.
Figure 3:
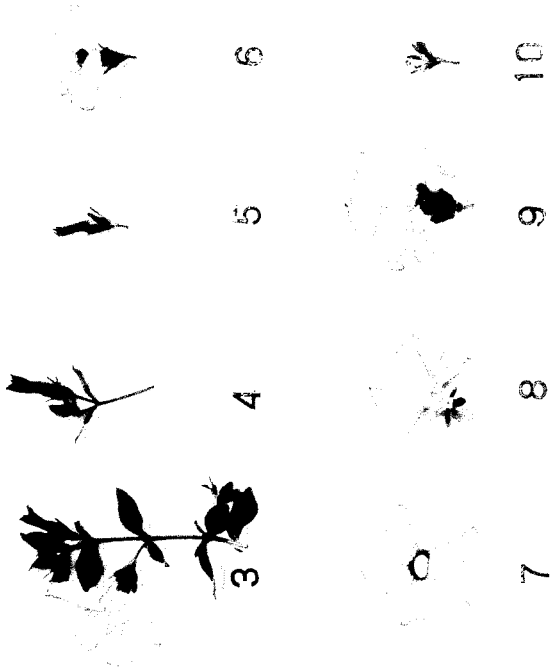
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and pistil and stamens (10), of the new variety of petunia plant.
Figure 4:
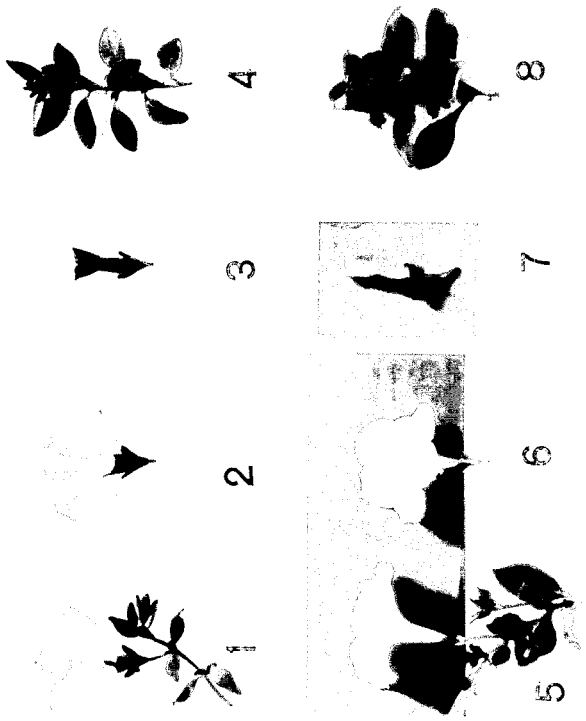
FIG. 4 is a photograph showing, in numerical order, a branch having an open flower (1), a flower (2), a bud (3), and a current shoot (4) of the new variety of petunia plant, in comparison with corresponding items (5–8) of a similar variety, 'Recoverer White'.

The botanical characteristics of the new and distinct variety of petunia plant 'Revolution Purplepink' are as follows.

Plant:

*Growth habit.*—Decumbent. The stems hang down when potted in a hanging pot.

*Plant height.*—15–20 cm.

*Spreading area of plant.*—The stem extends to a length of 50–80 cm from the base, and thus the spreading area of the plant is 100–150 cm in diameter.

*Growth.*—Very vigorous with abundant branching, a great profusion of blooms; the whole bush remaining in bloom for a considerable period of time.

*Blooming period.*—Late March to late September, in the southern Kantō area, Japan. The plant shape does not change throughout this period.

Stem:

*Thickness.*—Main stem 4.0–6.0 mm; lateral stem 2.0–3.0 mm.

*Color.*—Strong to moderate yellow green (R.H.S. 144B–143C, JHS 3512–3710).

*Pubescence.*—Normal.

*Branching.*—Over-abundant.

*Length of internode.*—1.0–1.5 cm before blooming; 3.0–4.0 cm during blooming.

Leaf:

*Phyllotaxis.*—Verticillate before blooming; opposite during blooming.

*Shape.*—Lancet.

*Size (average).*—7.5–8.0 cm×2.5–3.0 cm, large.

*Thickness.*—0.5–0.7 mm.

*Color.*—Moderate yellow green (R.H.S. 146B–137D, JHS 3508–3712).

*Pubescence.*—Normal.

Flower: Opening obliquely upward.

*Type.*—Single.

*Shape.*—Funnel-shape, with five-fissured limb.

*Diameter.*—8.0–9.0 cm, large.

*Color.*—In the unopened stage (bud), deep to moderate purple (R.H.S. 86A–83A, JHS 8307–8306); when open, vivid reddish purple (R.H.S. 74A, JHS 9207); at full bloom, vivid reddish purple (R.H.S. 71D–74B, JHS 9206–9207), with strong reddish purple (R.H.S. 72B, JHS 9208) lines radiating from a small brilliant purple (R.H.S. 82C, JHS 8611) area closely proximate to a pale to light yellow green (R.H.S. 4D–145C, JHS 3310–3103) center portion. The small area completely surrounds the center portion. The reverse side of the petal is a light purple color (R.H.S. 75B, JHS 8903). The petal has a somewhat metallic luster.

*Reproductive organs.*—1 normal pistil having a grayish yellow green (R.H.S. 138A, JHS 3715) stigma, and 5 normal stamens each having a moderate blue (R.H.S. 98B–98C, JHS 8305) anther and a purple yellow green (R.H.S. 145D, JHS 3502) filament.

*Peduncle.*—2.0 mm in thickness, and 2.0–2.5 cm in length.

Physiological and ecological characteristics: High resistance to rain, heat, and drought. Also high resistance to disease, particularly gray mold (Botrytis). Moderate resistance to pest.

This new variety of petunia plant is most suitable for flower bedding and potting, particularly in hanging pots or planters, and further excellent for ground cover.

The plant of this new variety 'Revolution Purplepink' is presently planted and maintained at the Yachiyo Farm of the Keisei Rose Nurseries, Inc., residing at 755 Ōwadasinden, Yachiyo-shi, Chiba-ken, Japan.

We claim:

1. A new and distinct variety of petunia plant, substantially as herein illustrated and described, characterized particularly as to novelty by (A) being a decumbent habit plant having long stems and large leaves, (B) an abundant branching and a great profusion of blooms, the whole bush remaining in bloom for a considerable period of time, (C) flowers that are single and large, the petals having a somewhat metallic luster and a vivid reddish purple color with strong reddish purple lines radiating from a small brilliant purple area closely proximate to a pale to light yellow green center portion, and (D) a high resistance to rain, heat, and drought.

* * * * *